US006727254B2

(12) United States Patent
Tulshian et al.

(10) Patent No.: US 6,727,254 B2
(45) Date of Patent: Apr. 27, 2004

(54) HETEROARYL TROPANE DERIVATIVES AS SUPERIOR LIGANDS FOR NOCICEPTIN RECEPTOR ORL-1

(75) Inventors: Deen Tulshian, Lebanon, NJ (US); Ginny D. Ho, Murray Hill, NJ (US); Fay W. Ng, New York, NY (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/288,976

(22) Filed: Nov. 6, 2002

(65) Prior Publication Data

US 2003/0119847 A1 Jun. 26, 2003

Related U.S. Application Data

(60) Provisional application No. 60/333,284, filed on Nov. 7, 2001.

(51) Int. Cl.[7] ............... C07D 401/04; C07D 403/04; A61K 31/46; A61P 11/14; A61P 25/03
(52) U.S. Cl. ............... 514/252.18; 514/253.04; 514/256; 514/269; 514/304; 544/295; 544/298; 544/335; 544/362; 546/125
(58) Field of Search ............... 514/252.18, 253.04, 514/256, 304, 269; 544/295, 335, 362, 298; 546/125

(56) References Cited

U.S. PATENT DOCUMENTS

| 5,352,707 A | 10/1994 | Pompni et al. |
| 6,262,066 B1 * | 7/2001 | Tulshian et al. ............ 514/299 |
| 6,455,527 B2 * | 9/2002 | Tulshian et al. ............ 514/249 |
| 2002/0018336 A1 * | 2/2002 | Stack et al. ................ 514/256 |

FOREIGN PATENT DOCUMENTS

| WO | WO 01/07050 | 2/2001 |

OTHER PUBLICATIONS

Sandosham et al., *Tetrahedron, 50* (1994) 275–84.
Fawzi et al, *Eur. J. Pharmacology, 336* (1997), pp. 233–242.
Hey, Bolser et al, *Brit. J. Pharmacology, 114* (1995), pp. 735–738.

McLeod et al, *Brit. J. Pharmacology, 132* (2001), pp. 1175–1178.

West et al, *Molecular Pharmacology, 38* (1990), pp. 610–613.

* cited by examiner

*Primary Examiner*—Mukund J. Shah
*Assistant Examiner*—Thomas McKenzie
(74) *Attorney, Agent, or Firm*—Anita W. Magatti

(57) ABSTRACT

Novel compounds of the formula

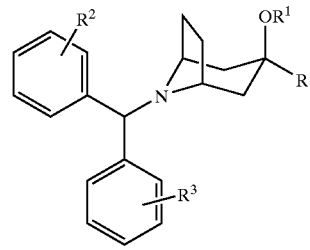

wherein

R is optionally substituted heteroaryl or

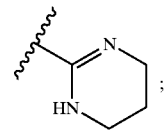

$R^1$ is H or $C_1$–$C_6$ alkyl; and $R^2$ and $R^3$ are —$CH_3$, —$OCH_3$ or halo;

or a pharmaceutically acceptable salt or solvate thereof, pharmaceutical compositions therefore, and the use of said compounds in the treatment of pain, anxiety, cough, asthma, depression and alcohol abuse are disclosed.

20 Claims, No Drawings

HETEROARYL TROPANE DERIVATIVES AS SUPERIOR LIGANDS FOR NOCICEPTIN RECEPTOR ORL-1

CROSS REFERENCE TO RELATED APPLICATION

This application claims the benefit of U.S. Provisional Application 60/333,284, filed Nov. 7, 2001.

BACKGROUND

The present invention relates to nociceptin receptor ORL-1 agonist 8-(bis-(halophenyl) methyl)-3-heteroaryl-8-azabicyclo-[3.2.1]octan-3-ols and derivatives thereof useful in treating cough, pain, anxiety, asthma, alcohol abuse or depression. Pharmaceutical compositions comprising the compounds and combinations of the claimed compounds with other agents for treating cough, allergy or asthma symptoms are also disclosed.

8-(bis-(halophenyl)methyl)-3-heteroaryl-8-azabicyclo-[3.2.1]octan-3-ols were generically, but not specifically, disclosed in U.S. Pat. No. 6,262,066 B1 and WO 01/07050 as being useful in the treatment of cough, pain, anxiety, asthma, alcohol abuse or depression. Compounds of the present invention represent a selection invention over U.S. Pat. No. 6,262,066 B1 and WO 01/07050.

SUMMARY OF THE INVENTION

Compounds of the present invention are represented by formula I

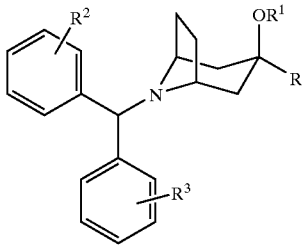

I or pharmaceutically acceptable salts thereof, wherein
R is $R^4$-heteroaryl or

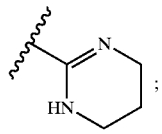

;

$R^1$ is H or $C_1$–$C_6$ alkyl;
$R^2$ and $R^3$ are independently selected from the group consisting of —$CH_3$, —$OCH_3$, fluoro, chloro, bromo and iodo;
$R^4$ is 1 to 4 substituents independently selected from the group consisting of H, halo, ($C_1$–$C_6$) alkyl, —CN, —$CF_3$, —$OCF_3$, —$(CH_2)_n$—$OR^5$, —$(CH_2)_n$—$NR^5R^6$, —$(CH_2)_n$—$NHSO_2R^5$, —$(CH_2)_n$—$NH(CH_2)_2NR^5R^6$, —$(CH_2)_n$—$NHC(O)NR^5R^7$, —$(CH_2)_n$—$NH(CH_2)_2$ $OR^5$ and 1-piperazinyl;
n is 0, 1, 2 or 3;
$R^5$ and $R^6$ are independently selected from the group consisting of H and $C_1$–$C_3$ alkyl; and
$R^7$ is H, $C_1$–$C_3$ alkyl or amino($C_1$–$C_3$)alkyl.

In another aspect, the invention relates to a pharmaceutical composition comprising at least one compound of formula I and a pharmaceutically acceptable carrier.

The compounds of the present invention are agonists of the ORL-1 receptor, and therefore, in another aspect, the invention relates to a method of treating pain, anxiety, cough, asthma, alcohol abuse or depression, comprising administering to a mammal in need of such treatment an effective amount of at least one compound of formula I.

In another aspect, the invention relates to a method of treating cough, comprising administering to a mammal in need of such treatment: (a) an effective amount of at least one compound of formula I; and (b) an effective amount of one or more additional agents for treating cough, allergy or asthma symptoms selected from the group consisting of: antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists.

In still another aspect, the invention relates to a pharmaceutical composition comprising at least one compound of formula I and one or more additional agents selected from the group consisting of: antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists.

DETAILED DESCRIPTION OF THE INVENTION

Referring to formula I, above, preferred compounds of the invention are those wherein $R^2$ and $R^3$ are in the 2-position on the phenyl rings. Also preferred are compounds wherein the same halo atom is selected for each of $R^2$ and $R^3$. More preferred are compounds wherein $R^2$ is chloro and $R^3$ is chloro, with compounds wherein $R^2$ is 2-chloro and $R^3$ is 2-chloro being most preferred.

Also preferred are compounds wherein R is $R^4$-heteroaryl wherein heteroaryl is pyridyl, pyrimidinyl, pyrazinyl, pyridazinyl, imidazolyl, pyrazolyl or indolyl, in particular 2-pyridyl or 2-pyrimidinyl. Preferred definitions of $R^4$ are hydrogen, ($C_1$–$C_6$) alkyl, —$OR^5$ and 1-piperazinyl. More preferred definitions of R are 2-pyrimidinyl, 5-ethyl-2 pyrimidinyl, 4-(1-piperazinyl)-2-pyrimidinyl, 2-pyridyl and 6-methoxy-2-pyridyl.

$R^1$ is preferably H or —$CH_3$, with H being more preferred.

The following individual compounds are especially preferred:

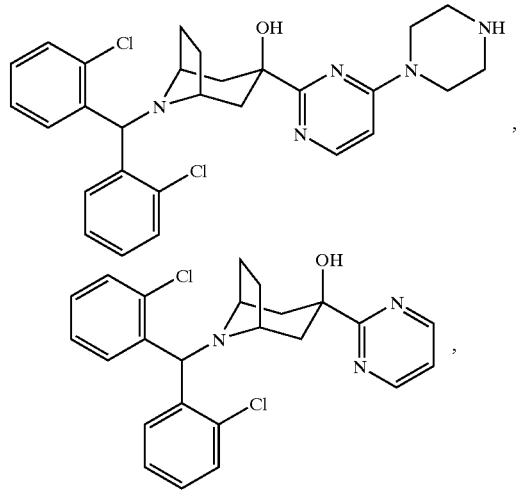

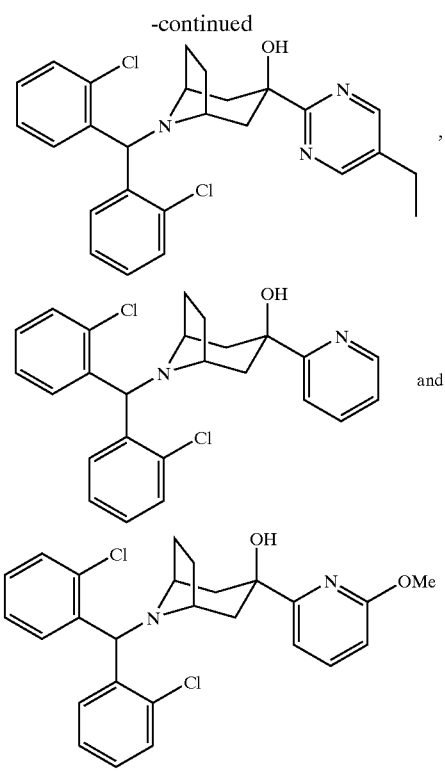

A preferred indication for compounds of formula I is for the treatment of cough.

As used herein, the following terms are used as defined below unless otherwise indicated:

halo represents fluoro, chloro, bromo and iodo;

heteroaryl represents cyclic aromatic groups of 5 or 6 atoms or bicyclic groups of 9 to 10 atoms having 1, 2 or 3 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. Nitrogen atoms can form an N-oxide. All regioisomers are contemplated, e.g., 2-pyridyl, 3-pyridyl and 4-pyridyl. Typical 6-membered heteroaryl groups are pyridyl, pyrimidinyl, pyrazinyl, pyridazinyl and the N-oxides thereof. Typical 5-membered heteroaryl rings are furyl, thienyl, pyrrolyl, thiazolyl, isothiazolyl, imidazolyl, pyrazolyl and isoxazolyl. Bicyclic groups typically are benzofused ring systems derived from the heteroaryl groups named above, e.g. quinolyl, phthalazinyl, quinazolinyl, benzofuranyl, benzothienyl and indolyl. The heteroaryl ring can be substituted with 1–4 $R^4$ groups, wherein any of the available substitutable carbon or nitrogen atoms in said heteroaryl group may be optionally and independently substituted.

Certain compounds of the invention may exist in different stereoisomeric forms (e.g., enantiomers, diastereoisomers and atropisomers). The invention contemplates all such stereoisomers both in pure form and in mixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of the invention can be prepared by known methods from starting materials either known in the art or prepared by methods known in the art.

A typical method for preparing the compounds of formula Ia wherein $R^1$ is H comprises reacting an 8-[bis-(halophenyl)methyl]-8-azabicyclo[3.2.1]octan-3-one of formula II with a lithium derivative of a heteroaryl:

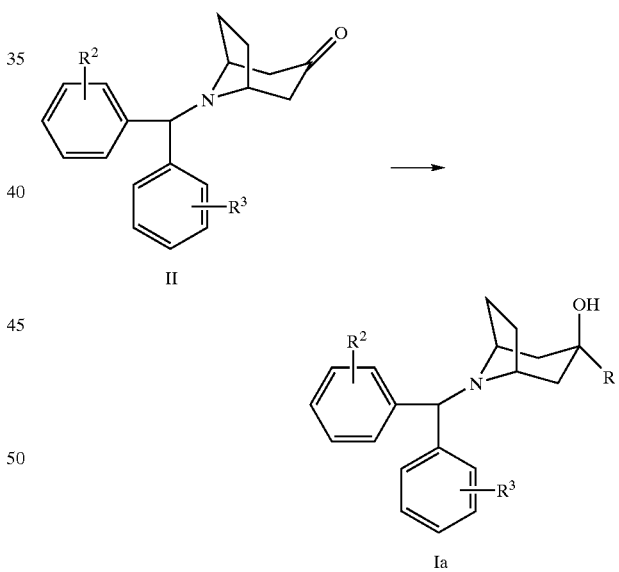

The starting material of formula II can be prepared according to the following reaction scheme:

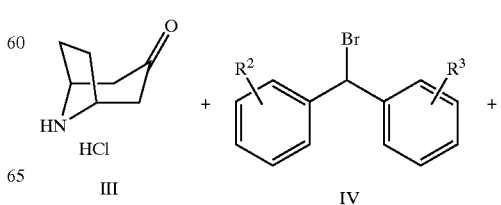

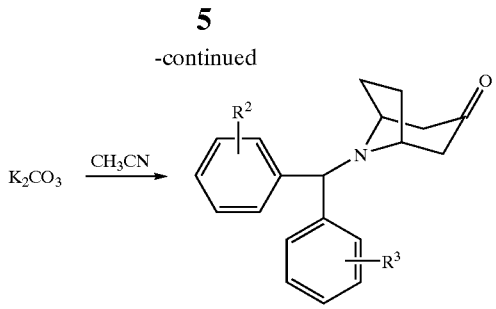

II

The compound of formula II can be prepared by alkylation of piperidine derivative III with diphenyl-bromomethane derivative IV in the presence of a base such as K₂CO₃, in a solvent such as CH₃CN, at 80° C. Compounds of formulas III and IV are known or can be prepared by known methods.

Compounds of the present invention and preparative starting materials thereof exemplified below should not be construed as limiting the scope of the disclosure.

The following solvents and reagents are referred to herein by the abbreviations indicated: tetrahydrofuran (THF); ethanol (EtOH); methanol (MeOH); ethyl acetate (EtOAc); lithium diisopropyl amide (LDA); triethylamine (Et₃N) and N,N-dimethylformamide (DMF). Room temperature is abbreviated as RT.

Preparation 1

8-Azabicyclo[3.2.1]octan-3-one, hydrochloride salt

Add α-chloroethyl chloroformate (15.4 g, 108 mmol) to a solution of tropinone (10 g, 71.84 mmol) in dichloroethane (200 ml) dropwise at 0° C. Heat the reaction to reflux for 2 h. Evaporate the solvent to produce a brown residue. Dissolve the residue in MeOH (200 ml) and heat it to reflux for 2 h. Evaporate the MeOH and stir the solid in EtOAc, filter, collect the solid and wash with ether to give the product (7 g). Crude product was used without further purification. $^1$H NMR (CDCl₃) δ4.45 (s, br, 2H), 3.35 (dd, 2H), 2.58 (d, 2H), 2.49 (dd, 2H), 2.0 (m, 2H).

Preparation 2

Bis(2-chlorophenyl)-bromomethane

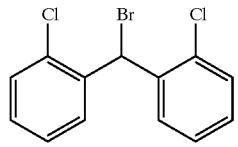

Step 1:
Add NaBH₄ (1.5 g, 39.82 mmol) to a solution of 2,2'-dichlorobenzophenone (5 g, 19.9 mmol) in MeOH (40 ml) at RT and stir for 2 h. Quench the reaction with H₂O, neutralize with 1N HCl and remove the MeOH. Extract the residue with EtOAc, wash with brine, dry over MgSO₄ and concentrate to give the desired compound (5 g) as white solid, which was used for next step reaction without purification. $^1$H NMR (CDCl₃) δ7.45 (m, 4H), 7.35 (m, 4H), 6.60 (d, 1H), 2.58 (d, 1H, OH).

Step 2:
Treat the product of Step 1 (20.36 g, 80.47 mmol) in CH₂Cl₂ with SOBr₂ (30.11 g, 144.85 mmol) at 0° C. and stir it at RT overnight. Quench the reaction with ice and NaHCO₃ (aq), extract with CH₂Cl₂, dry and filter. Remove the solvent to produce the desired bromide (23.6 g). $^1$H NMR (CDCl₃) δ7.6 (d, 2H), 7.4 (d, 2H), 7.13 (m, 4H), 7.0 (s, 1H).

Preparation 3

8-[Bis(2-chlorophenyl)methyl]-8-azabicyclo[3.2.1]octan-3-one

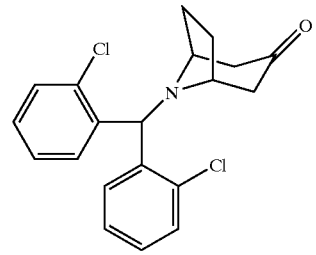

Heat a mixture of the products from Preparation 1 (26 g, 161 mmol) and Preparation 2 (53 g, 168 mmol) and K₂CO₃ (110 g, 796 mmol) in anhydrous CH₃CN (410 ml) to 80° C. for 80 h. Cool the reaction mixture to RT and filter. Evaporate the solvent and purify the solid by flash column chromatography (4%, 7% EtOAc/Hexane) to obtain the desired compound. $^1$H NMR (CDCl₃) δ7.9 (d, 2H), 7.3 (m, 4H), 7.2 (m, 2H), 5.7 (s,1H), 3.35 (s, br, 2H), 2.7 (dd, 2H), 2.3 (m, 2H), 2.2 (d, 2H), 1.65 (dd, 2H).

EXAMPLE 1

8-[Bis(2-chlorophenyl)methyl]-3-(2-pyrimidinyl)-8-azabicyclo[3.2.1]octan-3-ol

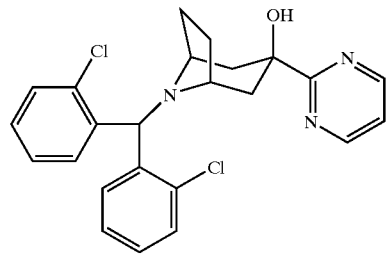

Step 1: 2-Tributylstannylpyrimidine
Prepare this compound according to the procedure described by Sandosham et al, *Tetrahedron* (1994), 50, 275–284). Prepare fresh LDA from diisopropyl amine (25 ml, 178 mmol) and n-BuLi (2.5 M, 70 ml, 175 mmol) in THF (230 ml). Treat the LDA solution with a solution of tributyltin hydride (142 ml, 156 mmol) in THF (30 ml) dropwise at 0° C. and stir for an additional 15 min after completion of addition. Cool the reaction mixture to −78° C., add a solution of 2-chloropyrimidine (15 g, 131 mmol) in THF (100 ml) dropwise and stir the reaction mixture for 3 h at −78° C., then allow the reaction mixture to warm to 0° C. over a period of 30 min. Pour the reaction mixture on saturated aqueous NH₄Cl and extract with EtOAc. Combine the organic layers, dry and concentrate. Purify the residue by column chromatography to produce the desired compound as a light yellow oil. ¹H NMR (CDCl₃) δ8.65 (d, 2H), 7.1 (t, 1H), 1.6 (m, 6H), 1.3 (m, 6H), 1.1 (m, 6H), 0.85 (t, 9H).

Step 2:

Add n-BuLi (2.5 M in hexane, 16.5 ml, 41.2 mmol) dropwise to the solution of the product of Step 1 (15 g, 40.6 mmol) in THF (80 ml) at −78° C. and maintain the reaction at this temperature for 45 min. To this solution, add a solution of the product of Preparation 3 (6 g, 16.7 mmol) in THF (30 ml) dropwise and stir the reaction mixture for additional 3 h at −78° C. Warm the reaction mixture to RT over a period of 1.5 h. Pour the reaction mixture on saturated aqueous NH₄Cl and extract with EtOAc. Combine the organic layers, dry and concentrate. Purify the residue by column chromatography to produce the title compound as light white solid. ¹H NMR (CDCl₃) δ8.75 (d, 2H), 7.96 (d, 2H), 7.30 (m, 4H), 7.20 (t, 1H), 7.15 (m, 2H), 5.59 (s, 1H), 4.86 (s, 1H, OH), 3.20 (m, br, 2H), 2.60 (dd, 2H), 2.40 (dd, 2H), 2.24 (m, 2H), 1.68 (d,2H).

EXAMPLE 2

8-[Bis(2-chlorophenyl)methyl]-3-(5-ethyl-2-pyrimidinyl)-8-azabicyclo[3.2.1]octan-3-ol

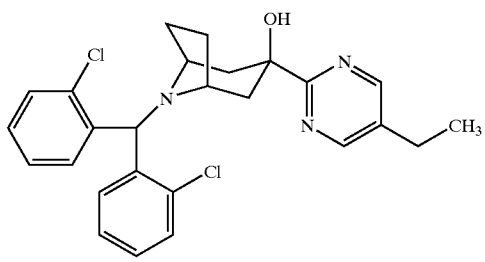

Step 1: 5-Ethtyl-2-tributylstannylpyrimidine

Using the procedure described in Example 1, Step 1, use LDA, tributyltin hydride (23.8 g, 81.78 mmol) and 2-chloro-5-ethylpyrimidine (10 g, 70 mmol)) to obtain the desired compound (6 g). ¹H NMR (CDCl₃) δ8.055 (s, 2H), 2.60 (q, 2H), 1.55 (m, 6H), 1.35 (m, 6H), 1.25 (t, 3H), 1.15 (t, 6H), 0.85 (t, 9H).

Step 2:

Add n-BuLi (2.5M, 6.5 ml, 16.33 mmol) dropwise to the solution of the product of Step 1 (5.9 g, 14.85 mmol) in THF at −78° C. and maintain the reaction at −78° C. for 30 minutes. To this, add the product from Preparation 3 (5.34 g, 14.85 mmol). Slowly warm the reaction mixture to RT and stir at RT overnight. Pour the reaction mixture into saturated aqueous NH₄Cl and extract with EtOAc. Combine the organic layers, dry and concentrate. Purify the residue by column chromatography to produce the title compound as white solid. ¹H NMR (CDCl₃) δ8.6(s, 2H), 8.0 (d, 2H), 7.25 (m, 4H), 7.15 (m, 2H), 5.6 (s, 1H), 4.85 (s, 1H, OH), 3.2 (s, br, 2H), 2.65 (q, 2H), 2.60 (d, 2H), 2.40 (m, 2H), 2.25 (m, 2H), 1.65 (d, 2H), 1.30 (t, 3H),

EXAMPLE 3

8-[Bis(2-chlorophenyl)methyl]-3-[4-(1-piperazinyl)-2-pyrimidinyl]-8-azabicyclo[3.2.1]octan-3-ol

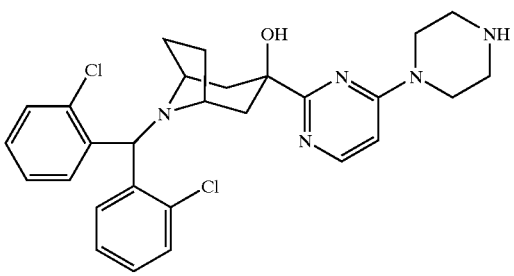

Step 1: 4-Chloro-2-tributylstannylpyrimidine

Using the procedure described in Example 1, Step 1, use LDA, tributyltin hydride (10.8 g, 37.2 mmol) and 2,4-dichloropyrimidine (5.2 g, 34.9 mmol)) to obtain the desired compound (6.3 g). ¹H NMR (CDCl₃) δ8.52 (d, 1H), 7.18 (d, 1H), 1.58 (m, 6H), 1.30 (q, 6H), 1.18 (t, 6H), 0.86 (t, 9H).

Step 2: 8-[Bis(2-chlorophenyl)methyl]-3-(4-chloro-2-pyrimidinyl)-8-azabicyclo-[3.2.1]octan-3-ol Add n-BuLi (2.5M, 8.0 ml, 20.0 mmol) dropwise to the solution of the product from Step 1 (6.3 g, 16.2 mmol) in THF (30 ml) at −78° C. and maintain the reaction at this temperature for 30 min. To this, add the product from Preparation 3 (4.0 g, 11.1 mmol). Slowly warm the reaction mixture to RT and stir at RT overnight. Pour the reaction mixture into saturated aqueous NH₄Cl and extract with EtOAc. Combine the organic layers, dry and concentrate. Purify the residue by column chromatography to produce the title compound as light brown foam. ¹H NMR (CDCl₃) δ8.61 (d, 1H), 7.93 (d, 2H), 7.25 (m, 5H), 7.12 (m, 2H), 5.65 (s, 1H), 4.33 (s, 1H, OH), 3.18 (s, br, 2H), 2.58 (dd, 2H), 2.33 (m, 2H), 2.13 (m, 2H), 1.65 (d, br, 2H).

Step 3:

Add piperazine (20 mg, 0.23 mmol) to a solution of the product of Step 2 (25 mg, 0.05 mmol) in EtOH (4 ml) at RT. Stir the reaction mixture at 80° C. overnight. Extract and purify to produce the title compound (20 mg). ¹H NMR (CDCl₃) δ8.24 (d, 1H), 7.93 (d, 2H), 7.26 (d, 2H), 7.22 (t, 2H), 7.10 (t, 2H), 6.33 (d, 1H), 5.64 (s, 1H), 3.67 (s, br, 4H), 3.15 (s, br, 2H), 2.95 (m, 4H), 2.59 (dd, 2H), 2.34 (m, 2H), 2.17 (m, 2H), 1.57 (d, br, 2H).

EXAMPLE 4

8-[Bis(2-Chlorophenyl)methyl]-3-(2-pyridinyl)-8-azabicyclo[3.2.1]octan-3-ol

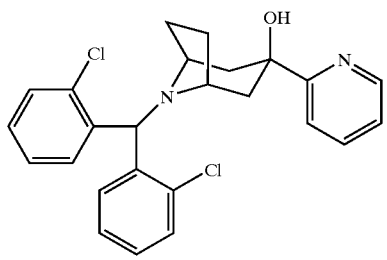

Add n-BuLi (2.5 M in hexane, 1.5 ml, 3.8 mmol) dropwise to a solution of 2-bromopyridine (0.50 g, 3.10 mmol) in THF (1 ml) at −78° C. and stir for 1 h. To this, add a solution of Preparation 3 (0.5 g, 1.4 mmol) in THF (1.5 ml) dropwise and stir the reaction mixture for an additional 3.5 h at −78° C. Warm the reaction mixture to 0° C. over a period of 1 h, pour the reaction mixture into saturated aqueous NH$_4$Cl and extract with EtOAc. Combine the organic layers, dry and concentrate. Purify the residue by column chromatography to produce the title compound as a pale yellow solid (400 mg). $^1$H NMR (CDCl$_3$) δ8.49 (d, 1H), 7.92 (d, 2H), 7.76 (t, 1H), 7.61 (d 1H), 7.28 (m, 4H), 7.16 (m, 3H), 5.65 (s, 1H), 5.54 (s, 1H, OH), 3.18 (s, br, 2H), 2.41 (m, 2H), 2.32 (dd, 2H), 2.21 (m, 2H), 1.72 (d, br, 2H).

EXAMPLE 5

8-[Bis(2-chlorophenyl)methyl]-3-(6-methoxy-2-pyridinyl)-8-azabicyclo[3.2.1]octan-3-ol

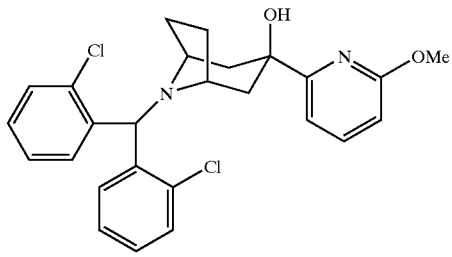

Add n-BuLi (2.5 M in hexane, 1.5 ml, 3.8 mmol) dropwise to a solution of 2-bromo-6-methoxypyridine (700 mg, 3.7 mmol) in THF (2 ml) at −78° C. and stir for 0.5 h. To this, add a solution of Preparation 3 (600 mg, 1.7 mmol) in THF (3 ml) dropwise and stir the reaction mixture for additional 1 h at −78° C. Warm the reaction mixture to 0° C. over a period of 2.5 h. Pour the reaction mixture into saturated aqueous NH$_4$Cl and extract with EtOAc. Combine the organic layers, dry and concentrate. Purify the residue by column chromatography to produce the title compound (0.5 g). ). $^1$H NMR (CDCl$_3$) δ7.90 (d, 2H), 7.65 (t, 1H), 7.31 (d, 2H), 7.26 (t, 2H), 7.13 (m, 3H), 6.63 (d, 1H), 5.64 (s, 1H), 5.15 (s, 1H, OH), 3.96 (s, 3H), 3.17 (s, br, 2H), 2.33 (m, 4H), 2.21 (m, 2H), 1.74 (d, br, 2H).

EXAMPLE 6

8-[Bis(2-chlorophenyl)methyl]-3-methoxy-3-(2-pyrimidinyl)-8-azabcyclo[3.2.1]octane

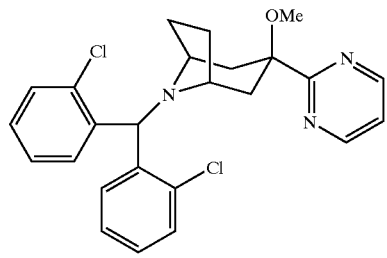

Treat the product of Example 1 (300 mg, 0.68 mmol) in THF (3ml) and DMF (1 ml) with NaH (30 mg, 0.75 mmol) at 0° C. for 30 min. Add CH$_3$I and warm the reaction mixture up to RT. After stirring overnight, quench the reaction mixture with H$_2$O, extract with EtOAc, wash with brine, dry and concentrate. Purify the resultant residue by column chromatography to obtain the title compound (0.25, g). $^1$H NMR (CDCl$_3$) δ8.77 (d, 2H), 7.83 (d, 2H), 7.27 (d, 2H), 7.18 (m, 3H), 7.10 (t, 2H), 5.54 (s, 1H), 3.15 (s, br, 2H), 2.99 (s, 3H), 2.38 (dd, 2H), 2.12 (m, 6H).

EXAMPLE 7

8-[Bis(2-chlorophenyl)methyl]-3-(1H-pyrazol-5-yl)-8-azabicyclo[3.2.1]octan-3-ol

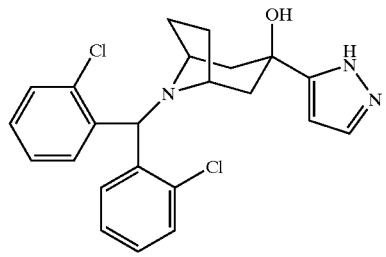

Add formaldehyde (37% wt, 1.5 ml, 50 mmol)) to pyrazole (0.68 g, 10 mmol) in water (4 ml) at RT, stir at RT overnight. Extract with CH$_2$Cl$_2$, dry (Na$_2$SO$_4$) and concentrate to give 1-hydroxymethylpyrazole. Add freshly prepared LDA (2.63 mmol) in THF to a solution of 1-hydroxymethylpyrazol (129 mg, 1.31 mmol) in THF (2 ml) at −78° C., stir at −20° C. for 40 min. and cool to −78° C. To this, add a solution of the product from Preparation 3 (236 mg, 0.65 mmol) in THF (3 ml) dropwise and stir the reaction mixture for additional 2 h at −78° C. Warm the reaction mixture to RT and stir overnight. Pour the reaction mixture into saturated aqueous NH$_4$Cl and extract with ether. Combine the organic layers, dry, filter and concentrate. Purify the residue by preparative thin layer chromatography and HPLC to produce the title compound (25 mg). $^1$H NMR (CDCl$_3$) δ8.2 (s, br, 2H), 8.05 (d, 2H), 7.25–7.40 (m, 6H), 7.20 (t, 2H), 6.2 (s, br, 1H), 5.9 (s, 1H), 3.2 (s, br, 2H), 2.55 (d, 2H), 2.41 (dd, 2H), 2.3 (m, 2H), 1.95 (d, 2H).

EXAMPLE 8

8-[Bis(2-chlorophenyl)methyl]-3-(1-methyl-pyrazol-5-yl)-8-azabicyclo[3.2.1]octan-3-ol

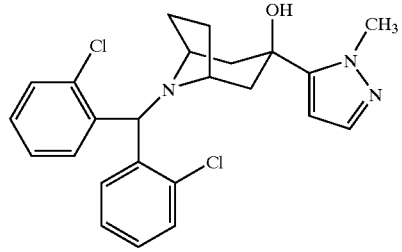

Add NaH (9.84 mg, 0.246 mmol) to a solution of Example 8 (70 mg, 0.164 mmol) in THF at 0° C. and stir for 30 min. Add CH$_3$I (34.89 mg, 0.246 mmol), warm to RT and stir overnight. Quench the reaction with saturated aqueous NH$_4$Cl, extract with EtOAc, dry (Na$_2$SO$_4$), filter and concentrate. Purify the residue by preparative thin layer chromatography to produce the title compound (51 mg). $^1$H NMR (CDCl$_3$) δ7.85 (d, 2H), 7.3 (m, 6H), 7.15 (t, 2H), 6.21 (s, 1H), 5.6 (s, 1H), 3.85 (s, 3H), 3.15 (s, br, 2H), 2.6 (s, 1H), 2.2–2.4 (m, 6H), 1.85 (d, 2H).

EXAMPLE 9

8-[Bis(2-chlorophenyl)methyl]-3-(1-methyl-1H-indol-2-yl)-8-azabicyclo[3.2.1]octan-3-ol

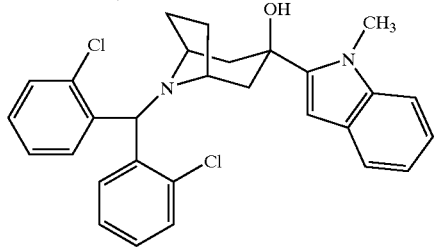

Add n-BuLi (1.6 M in hexane, 0.32 ml, 0.51 mmol) dropwise to a solution of 1-methylindole (67 mg, 0.51 mmol) in THF (2 ml) at −20° C., warm to RT, stir for 3.5 h and cool to −78° C. To this, add a solution of the product from Preparation 3 (92 mg, 0.26 mmol) in THF (2 ml). Warm the reaction mixture to RT and stir for 1.5 h. Pour the reaction mixture into saturated aqueous $NH_4Cl$ and extract with EtOAc. Combine the organic layers, dry and concentrate. Purify the residue by preparative thin layer chromatography to produce the title compound (5 mg). $^1H$ NMR ($CDCl_3$) δ7.80 (d, 2H), 7.60 (d, 1H), 7.05–7.35 (m, 9H), 6.45 (s,1H), 5.55 (s,1H), 3.20 (s, br, 2H), 2,55 (dd, 2H), 2.15 (br, s, 4H), 2.1 (d, 2H).

EXAMPLE 10

8-[Bis(2-chlorophenyl)methyl]-3-(1-methyl-1H-imidazol-2-yl)-8-azabicyclo[3.2.1]octan-3-ol

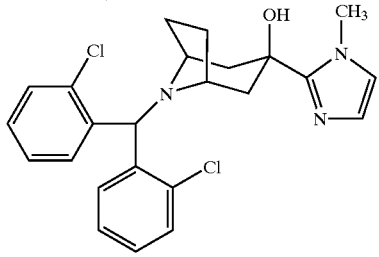

Add n-BuLi (2.5 M in hexane, 0.60 ml, 1.50 mmol) dropwise to a solution of 1-methylimidazole (0.15 g, 1.88 mmol) in THF (2 ml) at −78° C. and stir for 1.5 h. To this, add a solution of the product from Preparation 3 (0.20 g, 0.55 mmol) in THF (2 ml) dropwise and stir the reaction mixture for additional 2 h at −78° C. Warm the reaction mixture to ambient temperature for overnight, pour the reaction mixture into saturated aqueous $NH_4Cl$ and extract with EtOAc. Combine the organic layers, dry and concentrate. Purify the residue by column chromatography to produce the title compound as pale yellow solid (80 mg). $^1H$ NMR ($CDCl_3$) δ7.79 (d, 2H), 7.27 (d, 2H), 7.18 (t, 2H), 7.10 (t, 2H), 6.63 (d, 2H), 5.48 (s, 1H), 3.74 (s, 3H), 3.08 (br s, 2H), 2.45 (d, 2H), 2.14 (m, 4H), 1.81 (d, 2H).

EXAMPLE 11

8-[Bis(2-chlorophenyl)methyl]-3-(3-pyridazinyl)-8-azabicyclo[3.2.1]octan-3-ol

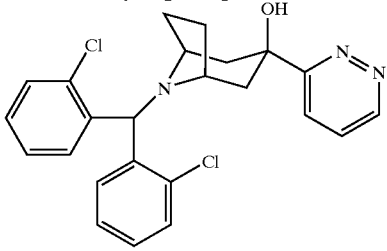

Add n-BuLi (2.5 M in hexane, 4.8 ml, 12.0 mmol) dropwise to a solution of 2,2,6,6-tetramethylpiperidine (1.67 g, 11.9 mmol) in THF (40 ml) at −78° C. and stir for 0.5 h. Warm the reaction mixture to 0° C. for 0.5 h. Cool the reaction mixture to −78° C., add a solution of pyridazine (0.94 g, 11.7 mmol) in THF (5 ml) dropwise and stir the reaction mixture for 15 min at −78° C. To this, add a solution of the product from Preparation 3 (1.0 g, 2.8 mmol) in THF (5 ml) dropwise and stir the reaction mixture for additional 1 h at −78° C. Warm the reaction mixture to ambient temperature for overnight. Pour the reaction mixture into saturated aqueous $NH_4Cl$ and extract with EtOAc. Combine the organic layers, dry and concentrate. Purify the residue by column chromatography to produce the title compound (300 mg). $^1H$ NMR ($CDCl_3$) δ9.10 (dd, 1H), 7.87 (d, 2H), 7.81 (dd, 1H), 7.53 (dd, 1H), 7.29 (d, 2H), 7.26 (t, 2H), 7.14 (t, 2H), 5.62 (s, 1H), 4.71 (br s, 1H), 3.20 (br s, 2H), 2.38 (m, 4H), 2.23)m, 2H), 1.80 (d, 2H).

EXAMPLE 12

8-[Bis(2-chlorophenyl)methyl]-3-(2-pyrazinyl)-8-azabicyclo[3.2.1]octan-3-ol

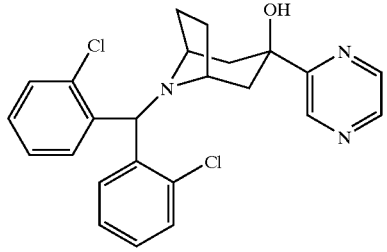

Add t-BuLi (1.7 M in pentane, 6.0 ml, 10.2 mmol) dropwise to a solution of iodopyrazine (1.0 g, 4.9 mmol) in diethyl ether (20 ml) at −50° C. and stir for 0.5 h. To this, add a solution of the product from Preparation 3 (1.0 g, 2.8 mmol) in THF (4 ml) dropwise and stir the reaction mixture for additional 1.5 h at −50° C. Warm the reaction mixture to ambient temperature for overnight. Pour the reaction mixture into saturated aqueous $NH_4Cl$ and extract with EtOAc. Combine the organic layers, dry and concentrate. Purify the residue by column chromatography to produce the title compound (400 mg). $^1H$ NMR ($CDCl_3$) δ8.96 (s, 1H), 8.47 (m, 2H), 7.89 (d, 2H), 7.29 (d, 2H), 7.27 (t, 2H), 7.14 (t, 2H), 5.63 (s, 1H), 4.34 (s, 1H), 3.20 (br s, 2H), 2.37 (m, 4H), 2.22 (m, 2H), 1.76 (d, 2H).

EXAMPLE 13

8-[Bis(2-chlorophenyl)methyl]-3-(4-pyrimidinyl)-8-azabicyclo[3.2.1]octan-3-ol

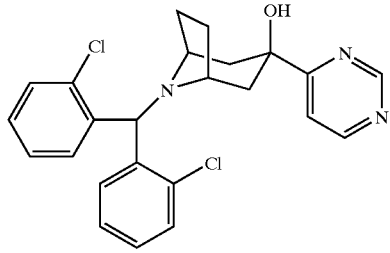

Step 1: 8-[Bis(2-chlorophenyl)methyl]-3-(5-bromo-4-pyrimidinyl)-8-azabicyclo-[3.2.1]octan-3-ol Add precooled (dry ice), freshly prepared LDA (2.77 mmol) in THF (5 ml) to a solution of 5-bromopyrimidine (450 mg, 2.77 mmol) and the product from Preparation 3 (1 g, 2.77 mmol) in THF (5 ml) dropwise and stir at RT overnight. Quench the reaction with ice-$H_2O$, extract with EtOAc, dry, filter and concentrate. Purify the residue by column chromatography to produce the desired compound (187 mg).

Step 2:

Hydrogenate the product of Step 1 (22 mg) in $CH_3OH$-EtOAc (1:1, 10 ml) and $NH_3/CH_3OH$ (7N, 1 ml) in the presence of Lindlar catalyst at 1 atm for 2 h, filter and concentrate to produce the title compound. $^1H$ NMR ($CDCl_3$) δ9.15 (s, 1H), 8.70 (d, 1H), 8.00 (m, 2H), 7.80 (d, 1H), 7.25 (m, 4H), 7.19 (t, 2H), 5.61 (s, 1H), 3.15 (br s, 2H), 2.50 (dd, 2H), 2.25 (m, 4H), 1.65 (d, 2H).

EXAMPLE 14

8-[Bis(2-chlorophenyl)methyl]-3-(5-bromo-2-pyridinyl)-8-azabicyclo[3.2.1]octan-3-ol

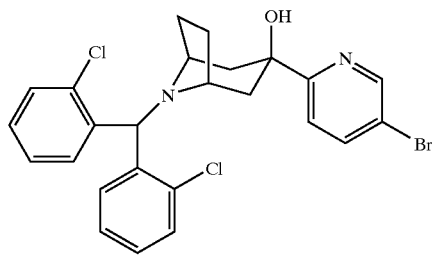

Add BuLi (1.6 M in hexane, 1.59 ml, 2.54 mmol) to 2,5-dibromopyridine (501 mg, 2.12 mmol) in toluene (13 ml) at −78° C. and stir for 2 h. Add the product from Preparation 3 (501 mg, 2.12 mmol) in toluene (2 ml) at −78° C. and stir for 3 h. Warm to RT, quench with saturated aqueous $NH_4Cl$, extract with $CH_2Cl_2$, dry and concentrate. Purify the residue by preparative thin layer chromatography and HPLC to give the title compound. $^1H$ NMR ($CDCl_3$) δ8.59 (s, 1H), 7.85 (m, 3H), 7.50 (d, 1H), 7.25 (m, 4H), 7.19 (t, 2H), 5.61 (s, 1H), 4.85 (s, 1H), 3.20 (br s, 2H), 2.15–2.40 (m, 4H), 1.75 (d, 2H).

EXAMPLE 15

1,1-Dimethylethyl [2-[[[[[6-[8-[bis(2-chlorophenyl)methyl]-3hydroxy-8-azabicyclo[3.2.1]-oct-3-yl]-2-pyridinyl]methyl]amino]carbonyl]amino]ethyl] carbamate

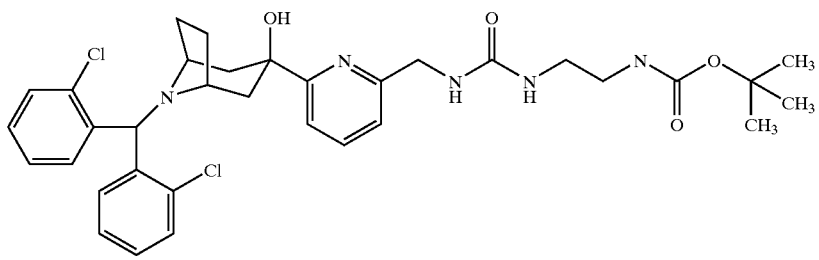

Step 1: 2-Bromo-6-hydroxymethylpyridine

Add $NaBH_4$ (1.46 g, 38.58 mmol) to 6-bromo-2-pyridine carboxylaldehyde (5.32 g, 28.58 mmol) in $CH_3OH$ at 0° C. and stir at 0° C. for 1 h, extract with $CH_2Cl_2$, dry over $Na_2SO_4$ and concentrate to give the desired compound.

Step 2: 2-Bromo-6-(t-butyldimethylsiloxymethyl)pyridine

Add imidazole (3.01 g, 44.19 mmol) to a solution of the product from Step 1 (5.54 g, 29.46 mmol) and t-butyldimethylsilyl chloride (4.97 g, 32.99 mmol) in $CH_2Cl_2$ (60 ml) at RT and stir overnight. Filter the reaction mixture and concentrate the filtrate. Purify the residue by chromatography to give the desired compound.

Step 3: 8-[Bis(2-chlorophenyl)methyl]-3-(6-(t-butyldimethylsiloxymethyl)-2-pyridinyl)-8-azabicyclo[3.2.1]octan-3-ol Add n-BuLi (1.6 M in hexane, 7.2 ml, 11.49 mmol) to the product from Step 2 (3.29 g, 10.88 mmol) in THF (5 ml) at δ78° C. and stir for 1 h. Add the product from Preparation 3 (1.84 g, 5.11 mmol) in THF (14 ml) at −78° C. and slowly warm to 0° C. (~2 h). Quench the reaction mixture with saturated aqueous $NH_4Cl$, extract with EtOAc, dry and concentrate. Purify the residue by column chromatography to give the desired compound.

Step 4: 8-[Bis(2-chlorophenyl)methyl]-3-(6-hydroxymethyl)-2-pyridinyl)-8-azabicyclo-[3.2.1octan-3-ol Add tetrabutylamonium fluoride (2.1 g, 8.04 mmol) to a solution of the product from Step 3 (2.34 g, 4.01 mmol) in THF (30 ml) at RT and stir overnight. Quench the reaction mixture with saturated aqueous $NaHCO_3$, extract with EtOAc, dry over $Na_2SO_4$ and concentrate. Purify the residue by column chromatography to give the desired compound.

Step 5: 3-[6-(Azidomethyl)-2-pyridinyl]-8-[Bis(2-chlorophenyl)methyl]-8-azabicyclo[3.2.1]octan-3-ol Add diphenylphosphoryl azide (272 mg, 0.99 mmol) and 1,8-diazabicyclo-[5,4,0]undec-7-ene (150 mg, 0.99 mmol) to the product from Step 4 (404 mg, 0.86 mmol) at 0° C., stir for 20 min., warm to RT then stir at 50° C. for 1 h. Cool to RT and stir overnight. Quench the reaction with $H_2O$ and saturated aqueous $NH_4Cl$, extract with $CH_2Cl_2$, dry and concentrate. Purify the residue by column chromatography to give the desired compound.

Step 6: 3-[6-(Aminomethyl)-2-pyridinyl]-8-[Bis(2-chlorophenyl)methyl]-8-azabicyclo-[3.2.1]octan-3-ol Add Lindlar catalyst (44 mg) to a suspension of the product from Step 5 (279 mg) in a mixture of EtOAc and CH₃OH in the presence of 7N NH₃ in CH₃OH (1 ml). Hydrogenate the mixture at 1 atm for 1.5 h, filter through celite, wash with NH₃/CH₃OH (3.5 N) and concentrate to give the desired compound.

Step 7:

Add triphosgene (34.8 mg, 0.117 mmol) and diisopropylethylamine (222 mg, 1.675 mmol) to a solution of the product from Step 7 (157 mg, 0.335 mmol) in toluene (10 ml) at RT under argon. Heat to 120° C. and stir for 2.5 h. Cool to RT, add N-Boc-ethylenediamine (65 mg, 0.42 mmol) and stir overnight. Quench the reaction with saturated aqueous NH₄Cl, extract with EtOAc, dry over Na₂SO₄ and concentrate. Purify the residue by preparative thin layer chromatography to give the title compound. ¹H NMR (CDCl₃) δ7.9 (d, 2H), 7.75 (t, 1H), 725 (d, 1H), 7.1–7.4 (m, 4H), 5.65 (s, 1H), 5.25 (b, s, 1H), 4.45 (d, 2H), 3.25 (m, 2H), 3.1 (m, 4H), 2.15–2.45 (m, 6H), 1.65 (d, 2H).

EXAMPLE 16

N-(2-(Aminoethyl)-N'-[[6-[8-[Bis(2-chlorophenyl) methyl]-3-hydroxy-8-azabicyclo[3.2.1]-oct-3-yl]-2-pyridinyl]methyl]urea

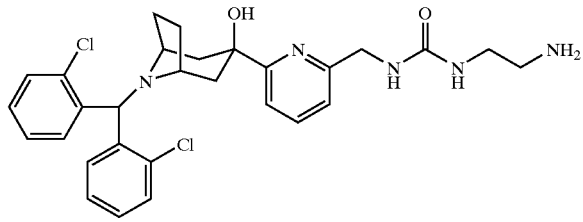

Add HCl (1N in ether, 1.0 ml) to a solution of Example 15 (53 mg) in CH₂Cl₂ and CH₃OH at RT and stir until LC-MS indicated the complete consumption of Example 15 to give the title compound as the hydrochloride salt. ESI-MS 554.1 (100, M⁺).

EXAMPLE 17

3-[3-(Aminomethyl)-2-pyridinyl]-8-[Bis(2-chlorophenyl)methyl]-8-azabicyclo[3.2.1]octan-3-ol

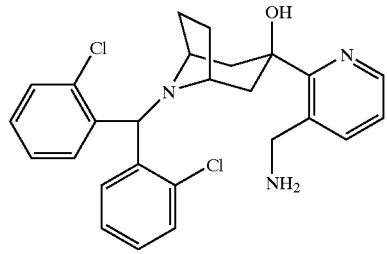

Step 1: 2-Bromo-3-hydroxymethylpyridine

Add ethyl chloroformate (3.17 g, 29.28 mmol) to a solution of 2-bromo-3-pyridinecarboxylic acid (5.63 g, 27.89 mmol) and Et₃N (2.96 g, 29.28 mmol) in toluene (150 ml) at RT and stir for 1 h., filter and concentrate. Dissolve the residue in THF (93 ml), add to a suspension of LiAlH₄ (1.11 g, 29.28 mmol) in THF (37 mmol) dropwise at −78° C. and stir for 30 min. Quench the reaction with saturated aqueous NH₄Cl, stir at RT for 1 h, filter through celite, extract with EtOAc, dry over Na₂SO₄ and concentrate. Purify the residue by column chromatography to produce the desired compound.

Step 2: 2-Bromo-3-(t-butyldimethylsiloxymethyl)pyridine

Follow the procedure of Step 2 of Example 15, using 2-bromo-3-hydroxy-methylpyridine (3.66 g, 19.48 mmol), t-butyldimethylsilyl chloride (5.87 g, 38.97 mmol) and imidazole (3.31 g, 48.71 mmol) to give the desire compound (6.38 g).

Step 3: 8-[Bis(2-chlorophenyl)methyl]-3-(3-(t-butyldimethylsiloxymethyl)-2-pyridinyl)-8-azabicyclo-[3.2.1]octan-3-ol Follow the procedure of Step 3 of Example 15, using the product from Step 2 (6.38 g, 21.1 mmol), n-BuLi (1.6 M in hexane, 14.5 ml, 21.1 mmol) and the product from Preparation 3 (7.60 g, 21.1 mmol) to give the desired product.

Step 4: 8-[Bis(2-chlorophenyl)methyl]-3-(3-hydroxymethyl)-2-pyridinyl)-8-azabicyclo-[3.2.1]octan-3-ol Follow the procedure of Step 4 of Example 15, using the product from Step 3 (12.3 g, 21.1 mmol) and tetrabutylamonium fluoride (11 g, 42.2 mmol) to give the desired compound.

Step 5: 3-[3-(Azidomethyl)-2-pyridinyl]-8-[Bis(2-chlorophenyl)methyl]-8-azabicyclo-[3.2.1]octan-3-ol Follow the procedure of Step 5 of Example 15, using the product from Step 4 (95.2 mg, 0.213 mmol), diphenylphosphoryl azide (67.4 mg, 0.245 mmol) and 1,8-diazabicyclo [5,4,0]undec-7-ene (52.96 mg, 0.32 mmol) to give the desired compound as the minor product.

Step 6:

Follow the procedure of Step 6 of Example 15, using the product from Step 5 (69 mg) and Lindlar catalyst (7 mg) to produce the title compound. ¹H NMR (CDCl₃) 8.40 (d, 1H), 7.95 (d, 2H), 775 (d, 1H), 7.05–7.15 (m, 7H), 5.60 (s, 1H), 5.25 (b, s, 1H), 4.40 (s, 2H), 3.20 (s, br, 2H), 2.50 (dd, 2H), 2.3 (m, 4H), 1.75 (d, 2H).

EXAMPLE 18

8-[Bis(2-chlorophenyl)methyl]-3-[4-(methylamino)-2-pyridinyl]-8-azabicyclo-[3.2.1]octan-3-ol

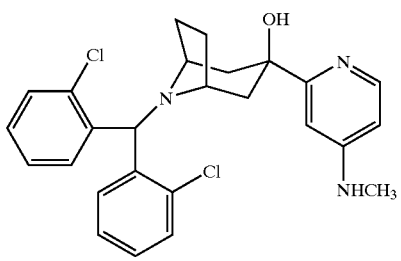

Step 1: 2-Bromo-4-(tert-Butoxycarbonylamino)pyridine

Stir a mixture of 4-amino-2-bromopyridine (1.00 g, 5.79 mmol), Et₃N (1.75 g, 17.37 mmol) and di-tert-butyl dicarbonate (1.90 g, 8.69 mmol) in CH₂Cl₂ (20 ml) at RT overnight. Dilute with CH₂Cl₂(10 ml), wash with saturated aqueous NaHCO₃, dry over MgSO₄ and concentrate. Purify the residue by column chromatography to give the desired compound.

Step 2:-Dimethylethyl [2-[8-[bis(2-chlorophenyl)methyl]-3-hydroxy-8-azabicyclo-3.2.1]-oct-3-yl]-4-pyridinyl] carbamate Add n-BuLi (1.6 M in hexane, 1.12 ml, 1.81 mmol) to the product from Step 1 (237 mg, 0.87 mmol) in THF (2.7 ml)

at −78° C. and stir for 2 h. Add the product from Preparation 3 (337 mg, 0.94 mmol) in THF (1 ml) at −78° C. and stir for 3 h, warm to RT and stir for overnight. Quench with saturated aqueous NH₄Cl, extract with EtOAc, dry and concentrate. Purify the residue by column chromatography to give the desired product.

Step 3:

Add LiAlH₄ (1 M in ether, 0.26 ml, 0.26 mmol) in dioxane (0.5 ml) to a solution of the product from Step 2 (48.4 mg, 0.087 mmol) in dioxane (0.5 ml) at RT and stir at reflux overnight. Cool to RT, add LiALH₄ (1.0 M in ether, 0.2 ml) and stir at reflux for 5 h. Quench the reaction with H₂O (0.05 ml), aqueous NaOH (15%, 0.1 ml) and H₂O (0.05 ml). Dilute with EtOAc, filter and concentrate. Purify the residue by column chromatography to produce the title compound. ¹H NMR (CDCl₃) 8.10 (d,1H), 7.95 (d, 2H), 7.05–7.15 (m, 6H), 6.75 (s, 1H), 6.39 (d, 2H), 5.70 (s, 1H), 3.20 (s, br, 2H), 2.95 (s, 3H), 2.35 (m, 4H), 2.2 (m, br, 2H), 1.65 (d, 2H).

EXAMPLE 19

3-[6-[(2-Aminoethyl)amino]-2-pyridinyl]-8-[bis(2-chlorophenyl)methyl]-8-azabicyclo[3.2.1]octan-3-ol

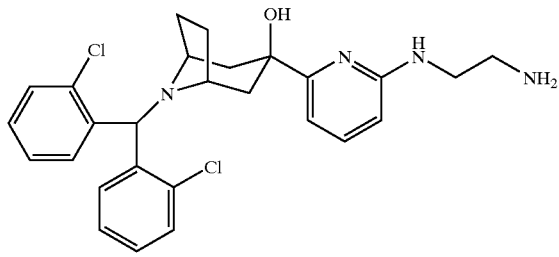

Step 1: 8-[Bis(2-chlorophenyl)methyl]-3-(6-bromo-2-pyridinyl)-8-azabicyclo[3.2.1]-octan-3-ol Add n-BuLi (1.6 M in hexane, 26.8 ml, 42.92 mmol) to 2,6-dibromopyridine (12.2 g, 51.5 mmol) in THF (150 ml) at −78° C. and stir for 2 h. Add the product from Preparation 3 (9.28 g, 25.75 mmol) in THF (50 ml) at −78° C. and stir for 3 h, warm to RT and stir overnight. Quench with saturated aqueous NH₄Cl, extract with EtOAc, dry and concentrate. Purify the residue by column chromatography to give the desired product.

Step 2: 1,1-Dimethylethyl [2-[6-[8-[bis(2-chlorophenyl)methyl]-3hydroxy-8-azabicyclo-[3.2.1]oct-3-yl]-2-pyridinyl]aminoethyl]carbamate Stir a solution of the product from Step 1 (64.5 mg, 0.128 mmol), N-Boc-ethylenediamine (123 mg, 0.77 mmol) and pyridine (12 mg, 0.154 mmol) at 110° C. in a sealed tube for 3.5 h. Cool to RT, add N-Boc-ethylenediamine (0.3 ml) and heat at 140° C. overnight. Cool to RT, quench the reaction with H₂O, extract with EtOAc, dry and concentrate. Purify the residue by column chromatography to give the desired product.

Step 3:

Add HCl (1N in ether, 0.36 ml) to a solution of the product from Step 2 (11 mg, 0.018 mmol) in CH₂Cl₂ at RT for 24 h. Add HCl (1N in ether, 0.36 ml) and stir at RT for 24 h. Add another 0.36 ml of HCl (1N in ether ) and stir at 30° C. for 24 h. Concentrate, treat with ether and filter to give the title compound as white solid. ESI-MS 497.1 (100, M⁺).

EXAMPLE 20

8-[Bis(2-chlorophenyl)methyl]-3-(1,4,5,6-tetrahydro-2-pyrimidinyl)-8-azabicyclo[3.2.1]octan-3-ol

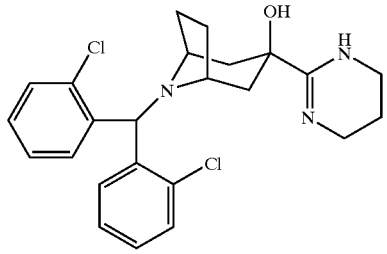

Add Raney nickel to a solution of Example 1 (160 mg) in ethanol (10 ml) at RT. Heat to 80° C. and stir for 20 h, filter and concentrate. Purify the residue by column chromatography to produce the title compound. ¹H NMR (CDCl₃) 7.85 (d, 2H), 7.25 (m, 4H), 7.15 (t, 2H), 5.55 (s, 1H), 3.40 (dd, 4H), 3.10 (s, br, 2H), 2.05–2.35 (m, 6H), 2.75(q, 2H), 1.55 (d, 2H).

The compounds of formula I exhibit greater than 50-fold selectivity over classical opioid receptors. The ORL-1 receptor shares a high degree of homology with classical opioid receptors (i.e., μ, κ and δ), but the ORL-1 receptor is not activated by endogenous opioids, and endogenous opioids do not activate the ORL-1 receptor. Codeine and other opioids used as cough suppressants are known to activate the mu-opioid receptor, causing side effects such as respiratory depression, constipation, tolerance and physical dependency. ORL-1 receptor agonists do not activate the mu-opioid receptor, and therefore are expected to result in a superior safety profile compared to opioids.

The ORL-1 receptor agonist activity of compounds of formula 1, and their effect on cough and respiration can be measured by the following tests.

Nociceptin Binding Assay

CHO cell membrane preparation expressing the ORL-1 receptor (2 mg) was incubated with varying concentrations of [¹²⁵I][Tyr¹⁴]nociceptin (3–500 pM) in a buffer containing 50 mM HEPES (pH7.4), 10 mM NaCl, 1 mM MgCl₂, 2.5 mM CaCl₂, 1 mg/ml bovine serum albumin and 0.025% bacitracin. In a number of studies, assays were carried out in buffer 50 mM tris-HCl (pH 7.4), 1 mg/ml bovine serum albumin and 0.025% bacitracin. Samples were incubated for 1 h at room temperature (22° C.). Radiolabelled ligand bound to the membrane was harvested over GF/B filters presoaked in 0.1% polyethyleneimine using a Brandell cell harvester and washed five times with 5 ml cold distilled water. Nonspecific binding was determined in parallel by similar assays performed in the presence of 1 μM nociceptin. All assay points were performed in duplicates of total and non-specific binding.

Calculations of Ki were made using methods well known in the art.

For compounds of this invention, Ki values were determined to be in the range of 0.6 to 30 nM, with compounds having a Ki value less than 10 nM being preferred.

Ki values for several exemplified compounds are shown in the following table:

| Example # | Ki (nM) |
|---|---|
| 1 | 6.2 |
| 2 | 7.6 |
| 3 | 4.0 |
| 4 | 4.0 |
| 6 | 5.4 |
| 8 | 6.0 |
| 11 | 7.0 |
| 12 | 2.0 |
| 14 | 1.3 |

Using the procedures described the *European Journal of Pharmacology*, 336 (1997), p. 233–242, the agonist activity of compounds of the invention was determined. The agonist activity ($EC_{50}$) of these compounds was measured to be in the range of 20–200 nM.

Cough Studies

The effects of a nociceptin agonist are evaluated in capsaicin-induced cough in the guinea pig according to the methods of Bolser et al. *British Journal of Pharmacology* (1995) 114, 735–738 (also see McLeod et al, *British Journal of Pharmacology* (2001) 132, 1175–1178). This model is a widely used method to evaluate the activity of potential antitussive drugs. Overnight fasted male Hartley guinea pigs (350–450 g, Charles River, Bloomington, Mass., USA) were placed in a 12"×14" transparent chamber. The animals were exposed to aerosolized capsaicin (300 μM, for 4 min) produced by a jet nebulizer (Puritan Bennett, Lenexa, Kans., USA) to elicit the cough reflex. Each guinea pig was exposed only once to capsaicin. The number of coughs were detected by a microphone placed in the chamber and verified by a trained observer. The signal from the microphone was relayed to a polygraph which provided a record of the number of coughs. Either vehicle (methylcellulose 1 ml/kg, p.o.) or test compound were given 2 hours before aerosolized capsaicin. The antitussive activity of baclofen (3 mg/kg, p.o.) was also tested as a positive control.

Respiratory Measurements

Studies were performed on male Hartley guinea pigs ranging in weight from 450 to 550 g. The animals were fasted overnight but given water and libitum. The guinea pigs were placed in a whole-body, head-out plethysmograph and a rubber collar was placed over the animal's head to provide an airtight seal between the guinea pig and the plethysmograph. Airflow was measured as a differential pressure across a wire mesh screen which covered a 1-in hole in the wall of the plethysmograph. The airflow signal was integrated to a signal proportional to volume using a preamplifier circuit and a pulmonary function computer (Buxco Electronics, Sharon, Conn., model XA). A head chamber was attached to the plethysmograph and air from a compressed gas source (21% $O_2$, balance $N_2$) was circulated through the head chamber for the duration of study. All respiratory measurements were made while the guinea pigs breathed this circulating air.

The volume signal from each animal was fed into a data acquisition/analysis system (Buxco Electronics, model XA) that calculated tidal volume and respiratory rate on a breath-by-breath basis. These signals were visually displayed on a monitor. Tidal volume and respiratory rate were recorded as an average value every minute.

The guinea pigs were allowed to equilibrate in the plethysmograph for 30 min. Baseline measurements were obtained at the end of this 30 min period. The guinea pigs were then removed from the plethysmograph and orally dosed with test compound (10 mg/kg, p.o.), baclofen (3 mg/kg, p.o.) or a methylcellulose vehicle placebo (2 ml/kg, p.o.). Immediately after dosing, the guinea pigs were placed into the plethysmograph, the head chamber and circulating air were reconnected and respiratory variables (tidal volume ($V_T$), respiratory rate (f) and minute volume ($MV=V_T \times f$)) were measured at 30, 60, 90 and 120 min post treatment. This study was performed under ACUC protocol #960103.

One to three compounds of formula I can be administered in the methods of this invention, preferably one.

Compounds of this invention exhibit anti-tussive activity, making them useful for suppressing coughing in mammals. For mammals treated for coughing, at least one nociceptin receptor ORL-1 agonist of formula I may be administered along with one or more additional agents for treating cough, allergy or asthma symptoms selected from antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists. Preferably a combination of this invention comprises one compound of formula I and 1–3 additional agents, preferably 1–2 additional agents, and more preferably 1 additional agent.

Non limitative examples of antihistamines include: astemizole, azatadine, azelastine, acrivastine, brompheniramine, certirizine, chlorpheniramine, clemastine, cyclizine, carebastine, cyproheptadine, carbinoxamine, descarboethoxyloratadine (also known as SCH-34117), doxylamine, dimethindene, ebastine, epinastine, efletirizine, fexofenadine, hydroxyzine, ketotifen, loratadine, levocabastine, mizolastine, equitazine, mianserin, noberastine, meclizine, norastemizole, picumast, pyrilamine, promethazine, terfenadine, tripelennamine, temelastine, trimeprazine and triprolidine.

Non-limitative examples of histamine $H_3$ receptor antagonists include: thioperamide, impromidine, burimamide, clobenpropit, impentamine, mifetidine, S-sopromidine, R-sopromidine, SKF-91486, GR-175737, GT-2016, UCL-1199 and clozapine. Other compounds can readily be evaluated to determine activity at $H_3$ receptors by known methods, including the guinea pig brain membrane assay and the guinea pig neuronal ileum contraction assay, both of which are described in U.S. Pat. No. 5,352,707. Another useful assay utilizes rat brain membranes and is described by West et al., "Identification of Two-$H_3$-Histamine Receptor Subtypes," *Molecular Pharmacology*, Vol. 38, pages 610–613 (1990).

The term "leukotriene inhibitor" includes any agent or compound that inhibits, restrains, retards or otherwise interacts with the action or activity of leukotrienes. Non-limitative examples of leukotriene inhibitors include montelukast [R-(E)]-1[[[1-[3-[2-(7-chloro-2-quinolinyl)-ethenyl] phenyl]-3[2-(1-hydroxy-1-methylethyl)phenyl] propyl]thio]-methyl]cyclo-propaneacetic acid and its sodium salt, described in EP 0 480 717; 1-(((R)-(3-(2-(6,7-difluoro-2-quinolinyl)ethenyl)phenyl)-3-(2-(2-hydroxy-2-propyl)-phenyl)thio) methylcyclopropaneacetic acid, and its sodium salt, described in WO 97/28797 and U.S. Pat. No. 5,270,324; 1-(((1(R)-3(3-(2-(2,3-dichlorothieno[3,2-b]-pyridin-5-yl)-(E)-ethenyl)phenyl)-3-(2-(1-hydroxy-1-methylethyl)phenyl) propyl)thio) methyl) cyclopropaneacetic acid, and its sodium salt, described in WO 97/28797 and U.S. Pat. No. 5,472,964; pranlukast, N-[4-oxo-2-(1 H-tetrazol-5-yl)-4H-1-benzopyran-8-yl]-p-

(4-phenylbutoxy) benzamide) described in WO 97/28797 and EP 173,516; zafirlukast, (cyclopentyl-3-[2-methoxy-4-[(o-tolylsulfonyl) carbamoyl]benzyl]-1-methyl-indole-5-carbamate) described in WO 97/28797 and EP 199,543; and [2-[[2(4-tert-butyl-2-thiazolyl)-5-benzofuranyl] oxymethyl] phenyl]acetic acid, described in U.S. Pat. No. 5,296,495 and Japanese patent JP08325265 A.

The term "5-lipoxygenase inhibitor" or "5-LO inhibitor" includes any agent or compound that inhibits, restrains, retards or otherwise interacts with the enzymatic action of 5-lipoxygenase. Non-limitative examples of 5-lipoxygenase inhibitors include zileuton, docebenone, piripost, ICI-D2318, and ABT 761.

Non-limitative examples of β-adrenergic receptor agonists include: albuterol, bitolterol, isoetharine, mataproterenol, perbuterol, salmeterol, terbutaline, isoproterenol, ephedrine and epinephrine.

A non-limitative example of a xanthine derivative is theophylline.

Non-limitative examples of α-adrenergic receptor agonists include arylalkylamines, (e.g., phenylpropanolamine and pseudephedrine), imidazoles (e.g., naphazoline, oxymetazoline, tetrahydrozoline, and xylometazoline), and cycloalkylamines (e.g., propylhexedrine).

A non-limitative example of a mast cell stabilizer is nedocromil sodium.

Non-limitative examples of anti-tussive agents include codeine, dextromethorphan, benzonatate, chlophedianol, and noscapine.

A non-limitative example of an expectorant is guaifenesin.

Non-limitative examples of $NK_1$, $NK_2$ and $NK_3$ tachykinin receptor antagonists include CP-99,994 and SR 48968.

Non-limitatve examples of $GABA_B$ agonists include baclofen and 3-aminopropyl-phosphinic acid.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably a compound of this invention is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to provide relief from pain, anxiety, depression, asthma or alcohol abuse. The compounds are non-toxic when administered within this dosage range.

When the nociceptin receptor ORL-1 agonist of formula I is administered in combination with one or more additional agents, the compound of formula I and the additional agent(s) are preferably administered in a combined dosage form (e.g., a single tablet), although they can be administered separately. The additional agents are administered in amounts effective to provide relief from cough, allergy or asthma symptoms, preferably from about 0.1 mg to 1000 mg, more preferably from about 1 mg to 300 mg per unit dose. A typical recommended dosage regimen of the additional agent is from 1 mg to 2000 mg/day, preferably 1 to 1000 mg/day, in two to four divided doses. Typical dosage amounts of the other agents may be determined from the literature, for example in The Physicians's Desk Reference.

The following are examples of pharmaceutical dosage forms which contain a compound of the invention. Those skilled in the art will recognize that such dosage forms can be easily modified to include one or more additional active ingredients. The scope of the invention in its pharmaceutical composition aspect is not to be limited by the examples provided.

Pharmaceutical Dosage Form Examples

Example A-Tablets

| No. | Ingredients | mg/tablet | mg/tablet |
|---|---|---|---|
| 1. | Active compound | 100 | 500 |
| 2. | Lactose USP | 122 | 113 |

-continued

| No. | Ingredients | mg/tablet | mg/tablet |
|---|---|---|---|
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|   | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B-Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|   | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the formula

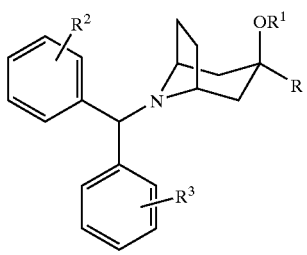

I or pharmaceutically acceptable salts thereof, wherein

R is $R^4$-heteroaryl or

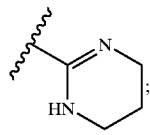

$R^1$ is H or $C_1$–$C_6$ alkyl;

$R^2$ and $R^3$ are independently selected from the group consisting of —$CH_3$, —$OCH_3$, fluoro, chloro, bromo and iodo;

$R^4$ is 1 to 4 substituents independently selected from the group consisting of H, halo, ($C_1$–$C_6$) alkyl, —CN, —$CF_3$, —$OCF_3$, —$(CH_2)_n$—$OR^5$, —$(CH_2)_n$—$NR^5R^6$, —$(CH_2)_n$—$NHSO_2\ _R{}^5$, —$(CH_2)_n$—$NH(CH_2)_2NR^5R^6$, —$(CH_2)_n$—$NHC(O)NR^5R^7$, —$(CH_2)_n$—$NH(CH_2)_2OR^5$ and 1-piperazinyl;

n is 0, 1, 2 or 3;

$R^5$ and $R^6$ are independently selected from the group consisting of H and $C_1$–$C_3$ alkyl; and $R^7$ is H, $C_1$–$C_3$ alkyl or amino($C_1$–$C_3$)alkyl.

2. A compound of claim 1 wherein R is $R^4$-pyrimidinyl or $R^4$-pyridyl.

3. A compound of claim 2 wherein R is 2-pyridyl or 2-pyrimidinyl.

4. A compound of claim 2 wherein $R^4$ is selected from the group consisting of ($C_1$–$C_6$) alkyl, —$OR^5$ and 1-piperazinyl.

5. A compound of claim 2 wherein R is 2-pyrimidinyl, 5-ethyl-2 pyrimidnyl, 4-(1-piperazinyl)-2-pyrimidinyl, 2-pyridyl or 6-methoxy-2-pyridyl.

6. A compound of claim 1 wherein $R^1$ is H or —$CH_3$.

7. A compound of claim 1 wherein $R^2$ and $R^3$ are in the 2-position on the phenyl rings.

8. A compound of claim 7 wherein $R^2$ is 2-chloro and $R^3$ is 2-chloro.

9. A compound of claim 1 selected from the group consisting of

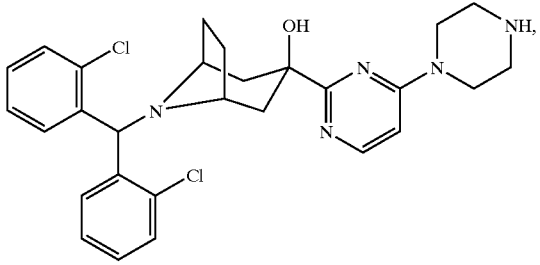

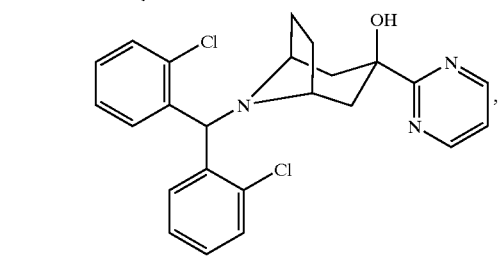

-continued

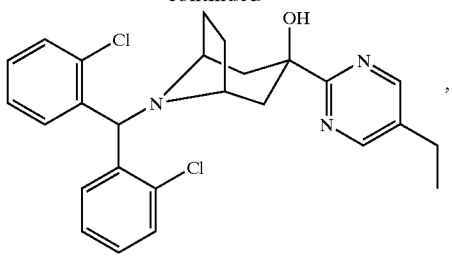

,

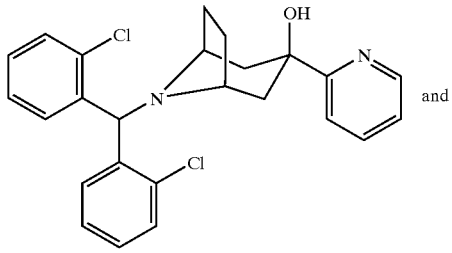

and

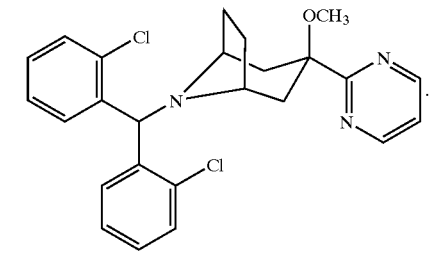

10. A compound represented by the formula:

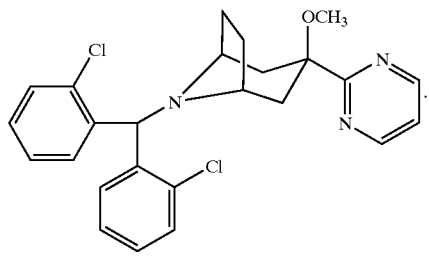

.

11. A pharmaceutical composition comprising a therapeutically effective amount of at least one compound of claim 1 in combination with a pharmaceutically acceptable carrier.

12. A pharmaceutical composition comprising: a therapeutically effective amount of at least one compound of claim 1; a therapeutically effective amount of one or more additional agents selected from the group consisting of: antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists; and a pharmaceutically acceptable carrier.

13. A method of treating cough, pain, anxiety, asthma, depression or alcohol abuse comprising administering an effective amount of at least one compound of claim 1 to a mammal in need of such treatment.

14. A method of treating cough comprising administering an effective amount of at least one compound of claim 1 to a mammal in need of such treatment.

15. The method of claim 14, wherein in addition to the compound of claim 1, an effective amount of 1–3 additional agents for treating cough, allergy or asthma symptom selected from the group consisting of: antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists is administered.

16. A pharmaceutical composition comprising a therapeutically effective amount of the compound of claim 10 in combination with a pharmaceutically acceptable carrier.

17. A pharmaceutical composition comprising: a therapeutically effective amount of the compound of claim 10; a therapeutically effective amount of one or more aditional agents selected from the group consisting of: antihistamines 5-lipoxygenase inhibitors, leukotriene inhibitors, $H_3$ inhibitors, β-adrenergic receptor agonists, xanthine derivatives, α-adrenergic receptors, mast cell stabilizers, anti-tussives, expectorants, $NK_1$, $NK_2$ and $NK_3$ tachykinin receptor antagonists, and $GAGA_B$ agonists; and a pharmaceutically acceptable carrier.

18. A method of treating cough, pain, anxiety, asthma, depression or alcohol abuse comprising administering an effective amount of the compound of claim 10 to a mammal in need of such treatment.

19. A method of treating cough comprising administering an effective amount of the compound of claim 10 to a mammal in need of such treatment.

20. The method of claim 19, wherein in addition to the compound of claim 10, an effective amount of 1–3 additional agents for treating cough, allergy or asthma symptoms selected from the group consisting of: antihistamines, 5-lipoxygenase inhibitors, leukotriene inhibitors, $H_3$ inhibitors, β- adrenergic receptor agonists, xanthine derivatives, α-adrenergic receptor agonists, mast cell stabilizers, anti-tussives, expectorents, $NK_1$, $NK_2$ and $NK_3$ tachykinin receptor antagonists, and $GABA_B$ agonists is adminstered.

* * * * *